US010695917B2

(12) United States Patent
Choi et al.

(10) Patent No.: US 10,695,917 B2
(45) Date of Patent: Jun. 30, 2020

(54) ONE-DEGREE-OF-FREEDOM LINK DEVICE, A ROBOT ARM USING THE SAME AND A SURGICAL ROBOT COMPRISING THE SAME

(71) Applicant: Industry-University Cooperation Foundation Hanyang University ERICA Campus, Gyeonggi-do (KR)

(72) Inventors: Youngjin Choi, Gyeonggi-do (KR); Byung-Ju Yi, Gyeonggi-do (KR); Hoyul Lee, Busan (KR)

(73) Assignee: Industry-University Cooperation Foundation Hanyang University ERICA Campus, Gyeonggi-do (KR)

( * ) Notice: Subject to any disclaimer, the term of this patent is extended or adjusted under 35 U.S.C. 154(b) by 227 days.

(21) Appl. No.: 15/883,861

(22) Filed: Jan. 30, 2018

(65) Prior Publication Data
US 2018/0161990 A1    Jun. 14, 2018

Related U.S. Application Data

(62) Division of application No. 13/638,370, filed as application No. PCT/KR2011/002206 on Mar. 31, 2011, now Pat. No. 9,919,433.

(30) Foreign Application Priority Data

Mar. 31, 2010  (KR) .......................... 10-2010-0029233
Mar. 31, 2010  (KR) .......................... 10-2010-0029236

(51) Int. Cl.
*B25J 17/00*     (2006.01)
*B25J 9/10*      (2006.01)
(Continued)

(52) U.S. Cl.
CPC ............... *B25J 17/00* (2013.01); *A61B 34/30* (2016.02); *A61B 34/37* (2016.02); *A61B 34/71* (2016.02);
(Continued)

(58) Field of Classification Search
CPC ............................... B25J 9/1065; B25J 9/106
See application file for complete search history.

(56) References Cited

U.S. PATENT DOCUMENTS 4,776,230 A    10/1988  Susnjara
5,060,532 A    10/1991  Barker
(Continued)

FOREIGN PATENT DOCUMENTS

JP        10-122321      5/1998
KR     10-2007-0027695   3/2007
(Continued)

OTHER PUBLICATIONS

International Search Report for Application No. PCT/KR2011/002206 dated Dec. 19, 2011.

*Primary Examiner* — Terence Boes
(74) *Attorney, Agent, or Firm* — Womble Bond Dickinson (US) LLP

(57) ABSTRACT

The present invention comprises: a fixed four-node link in which four links are joined together in a hinged fashion, comprising a fixed link of which the position is fixed, a connecting rod positioned on the opposite side of the first link, an input-side transmission link connecting the end on one side of the connecting rod and the first link, and an output-side transmission link positioned on the opposite side of the input-side transmission link; an input link part to which an actuator is attached, and which is joined in hinged fashion between the two ends of the input-side transmission link; and an output link part which is fixedly joined to the
(Continued)

output-side transmission link and is rotated by means of the output-side transmission link, and the one-degree-of-freedom link device according to the present invention and the robot arm using the same can be used to allow easy attachment and detachment between link devices and achieve smooth action in a robot arm in accordance with what is desired.

14 Claims, 8 Drawing Sheets

(51) Int. Cl.
  *B25J 9/16*     (2006.01)
  *A61B 34/00*    (2016.01)
  *A61B 34/30*    (2016.01)
  *A61B 34/37*    (2016.01)
  *A61B 17/00*    (2006.01)
  *A61B 17/29*    (2006.01)
  *A61B 90/50*    (2016.01)

(52) U.S. Cl.
  CPC ............. *B25J 9/106* (2013.01); *B25J 9/1689* (2013.01); *A61B 2017/00327* (2013.01); *A61B 2017/2908* (2013.01); *A61B 2034/302* (2016.02); *A61B 2090/506* (2016.02); *Y10S 901/28* (2013.01); *Y10T 74/20329* (2015.01)

(56) References Cited

U.S. PATENT DOCUMENTS

| | | |
|---|---|---|
| 5,379,664 A | 1/1995 | Kershaw et al. |
| 7,568,880 B2 | 8/2009 | Horie et al. |
| 8,317,453 B2 | 11/2012 | Givens |
| 8,761,927 B2 | 6/2014 | Johnson et al. |
| 2003/0066373 A1 | 4/2003 | Maeguchi et al. |
| 2004/0024385 A1 | 2/2004 | Stuart |
| 2005/0096502 A1 | 5/2005 | Khalili |
| 2005/0262959 A1 | 12/2005 | Angeles et al. |
| 2008/0028883 A1 | 2/2008 | Inada et al. |
| 2009/0234369 A1 | 9/2009 | Bax et al. |
| 2010/0047051 A1 | 2/2010 | Knobel |
| 2012/0067156 A1 | 3/2012 | Chen et al. |
| 2014/0180309 A1 | 6/2014 | Seeber et al. |

FOREIGN PATENT DOCUMENTS

| | | | |
|---|---|---|---|
| KR | 10-0695471 | 3/2007 | |
| KR | 2009-0124552 | 12/2009 | |
| SU | 1038219 A1 * | 8/1983 | ............ B25J 9/1065 |
| WO | 2009/145388 | 12/2009 | |

* cited by examiner

【Figure 1a】
PRIOR ART
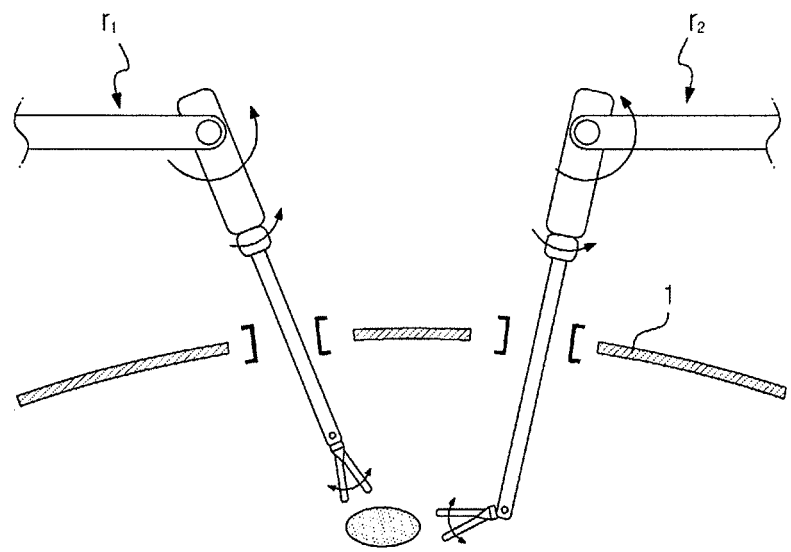
【Figure 1b】
PRIOR ART
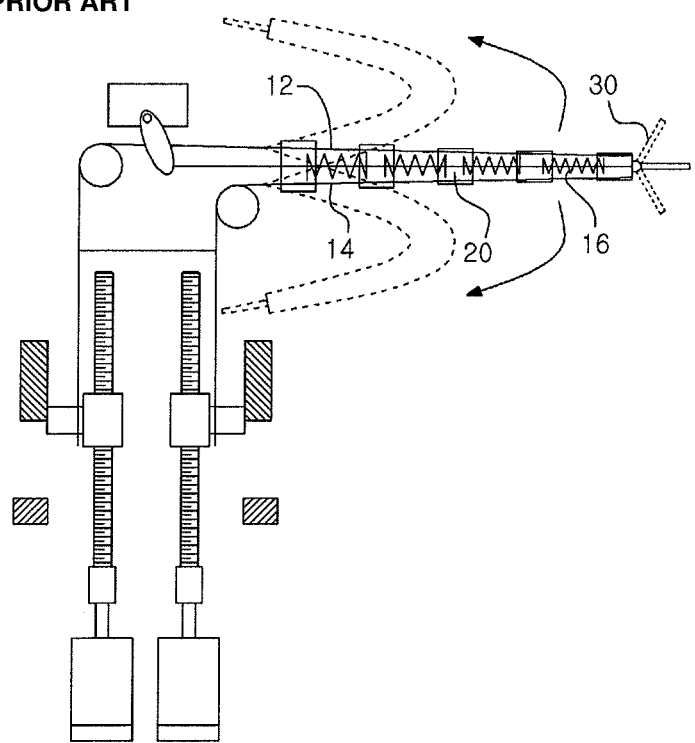

[Figure 2]
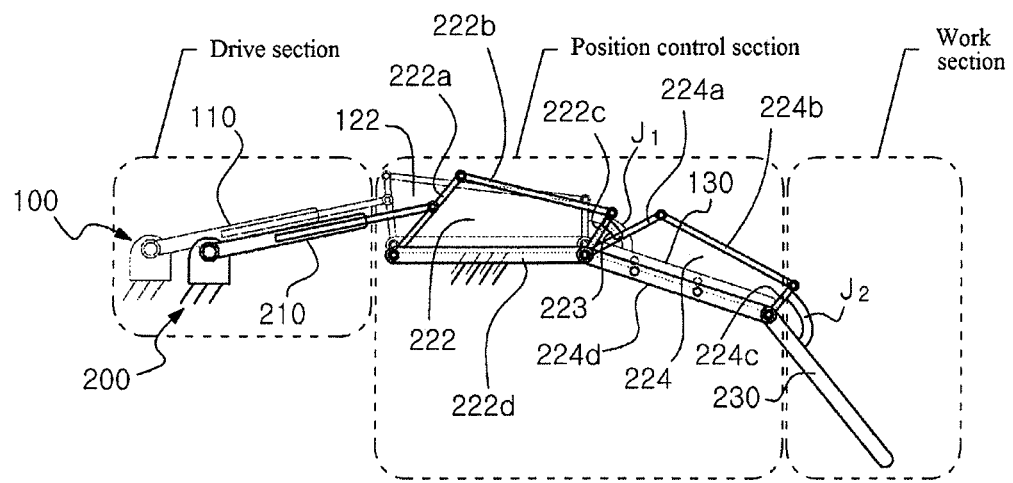
[Figure 3]
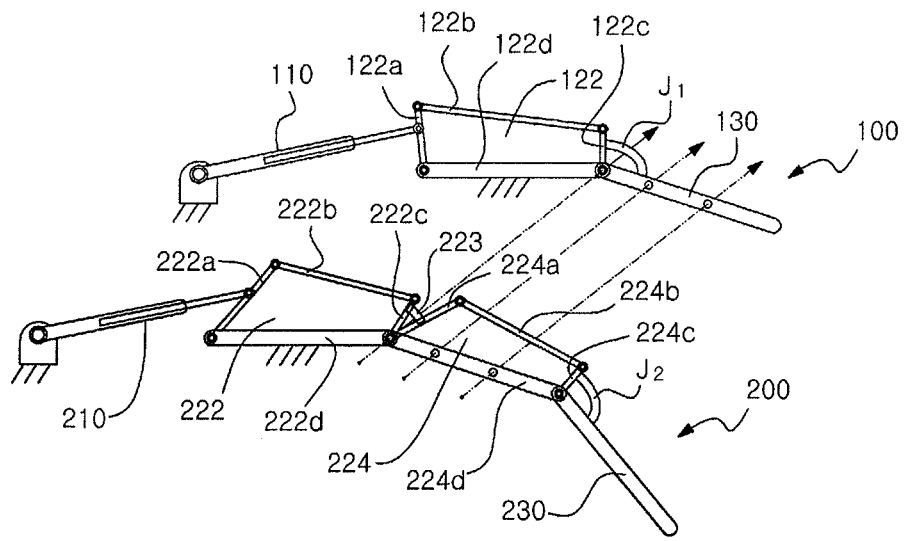

[Figure 4]
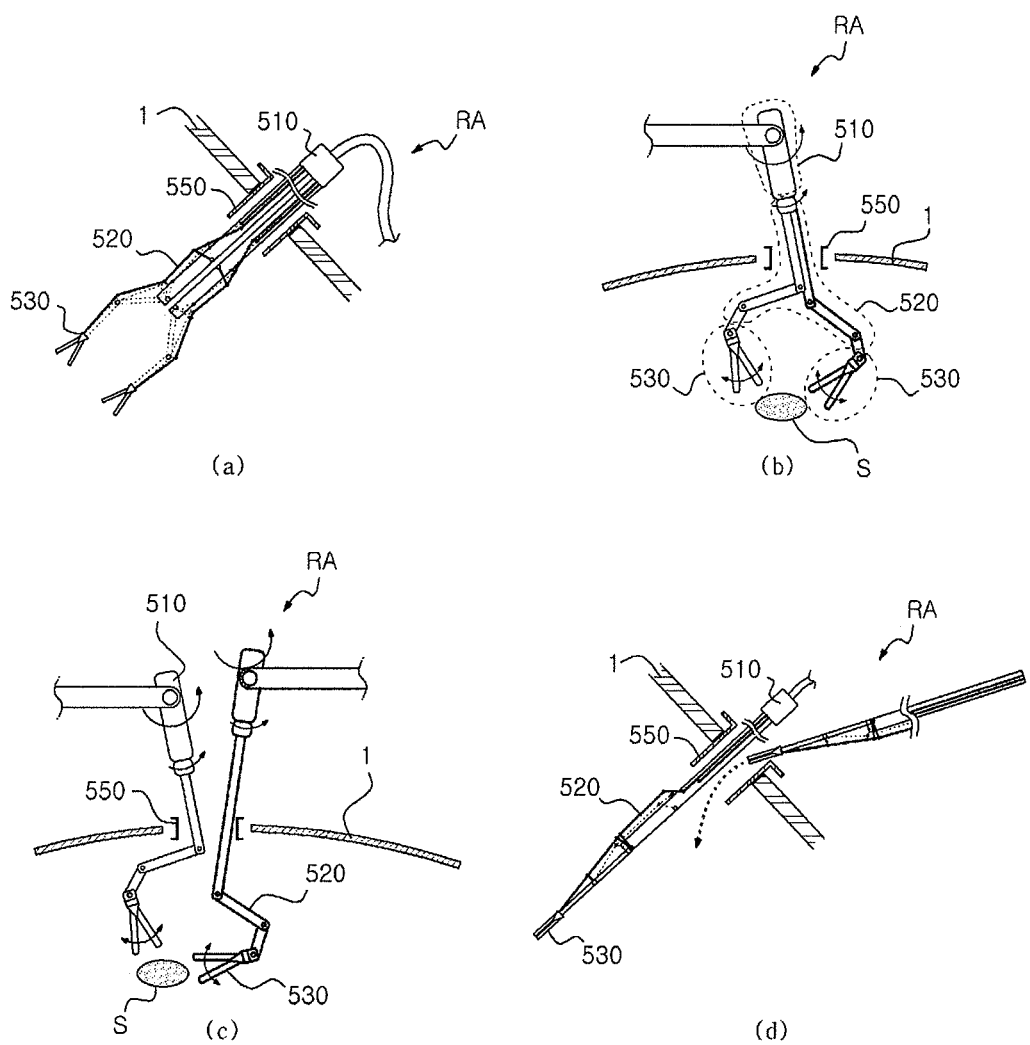

[Figure 5]
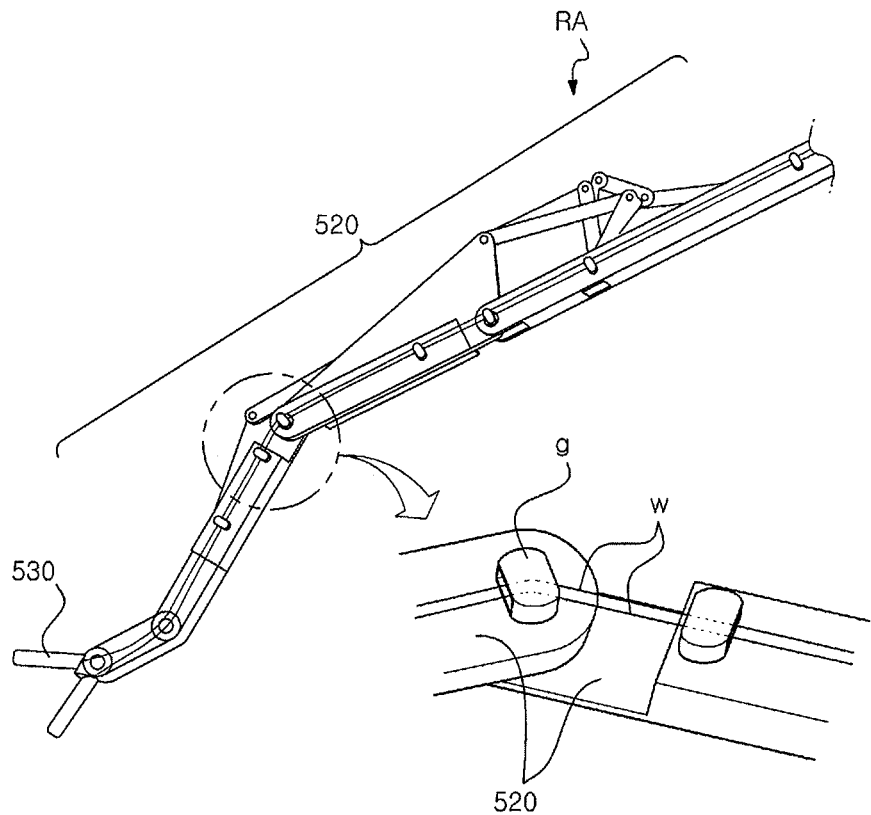
[Figure 6]
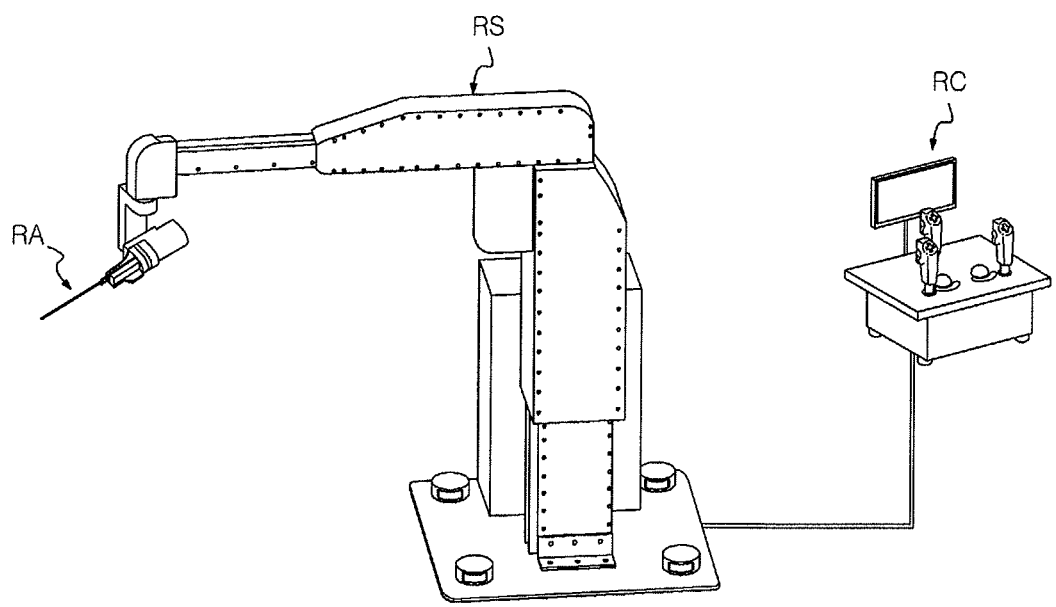

[Figure 7]
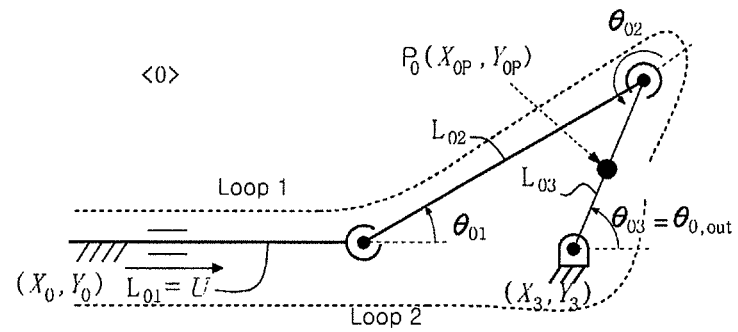
(a)
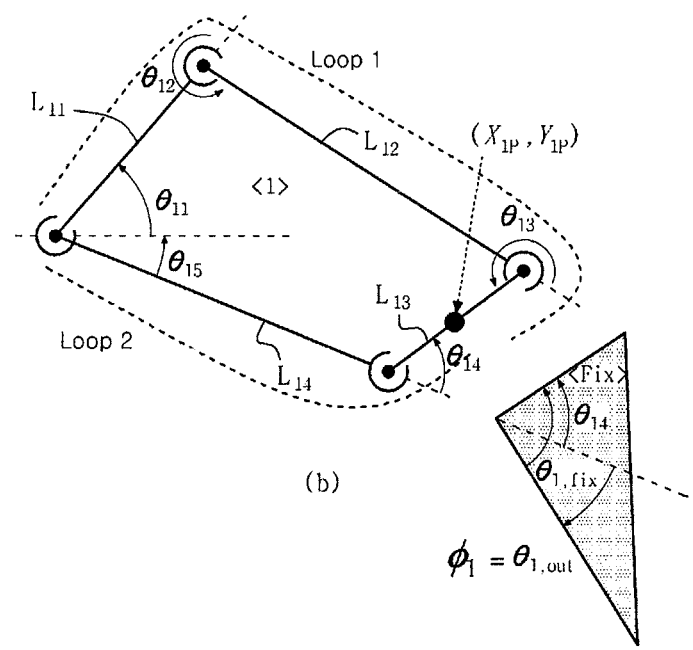
(b)

[Figure 8]
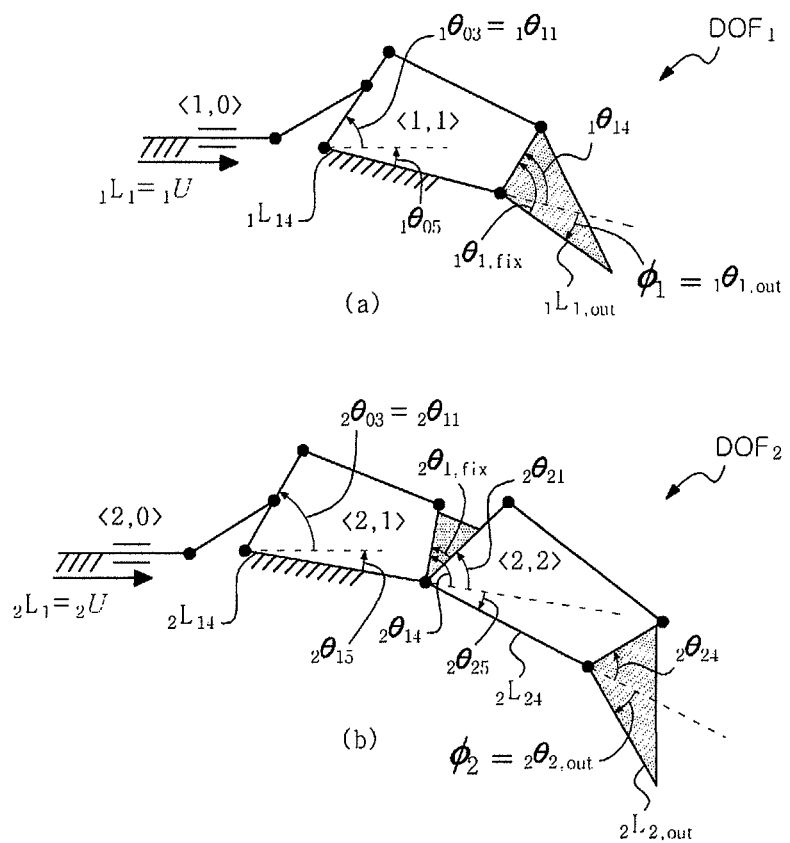

[Figure 9]
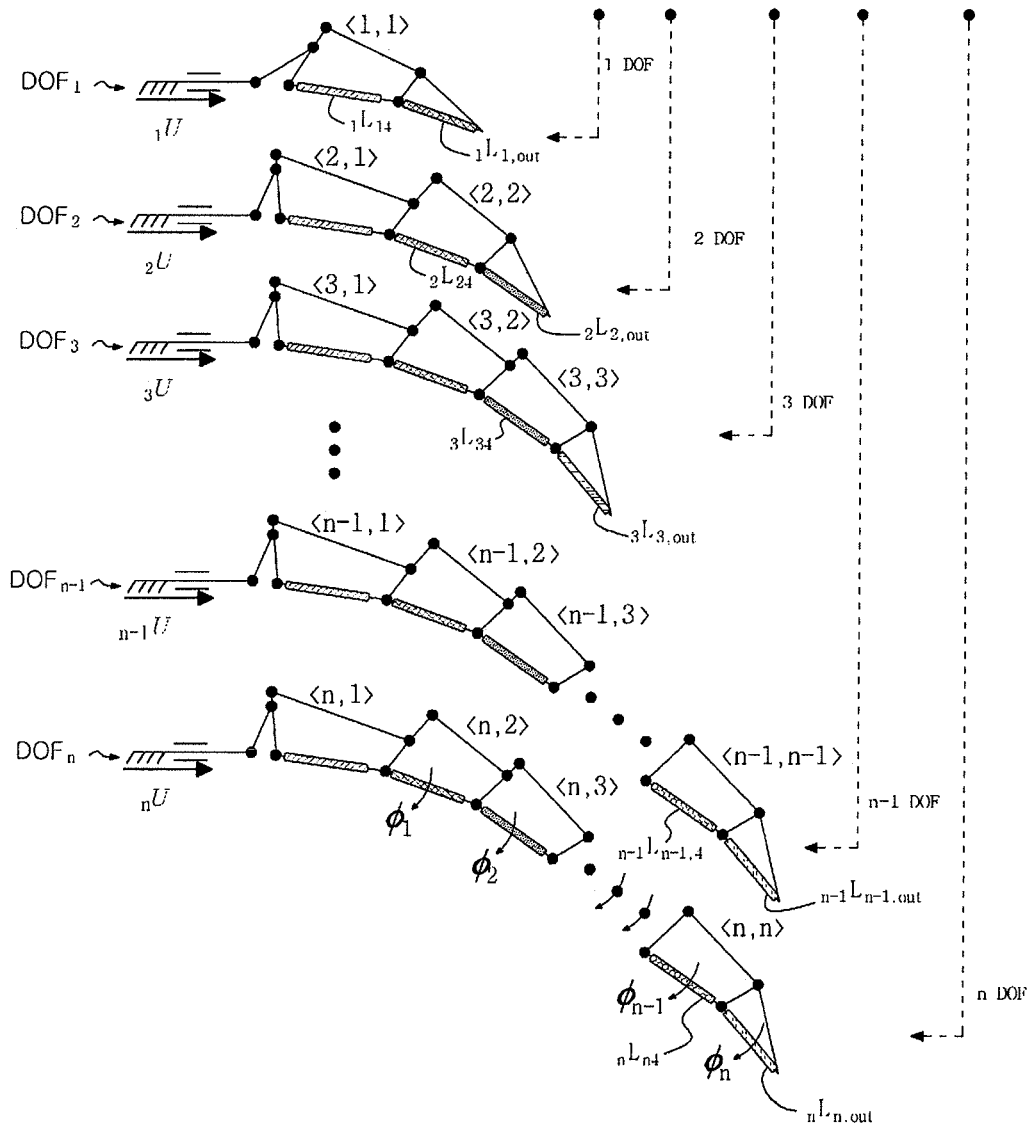

【Figure 10】
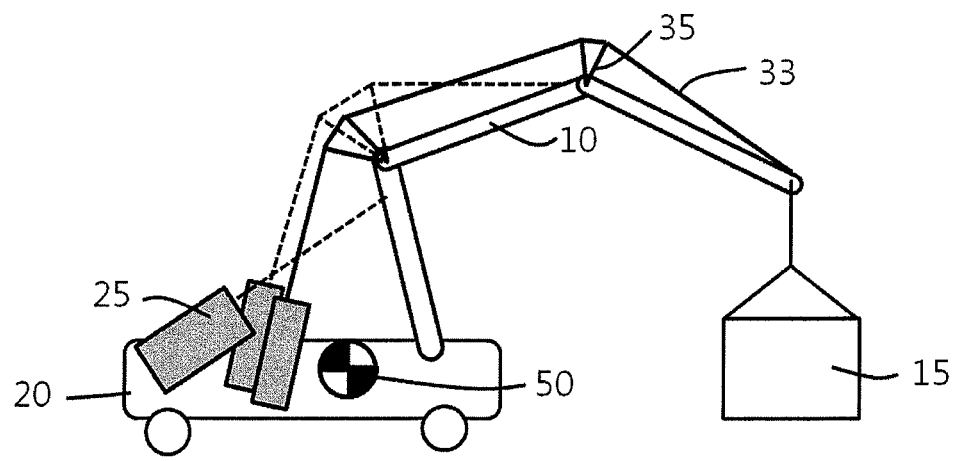

ONE-DEGREE-OF-FREEDOM LINK DEVICE, A ROBOT ARM USING THE SAME AND A SURGICAL ROBOT COMPRISING THE SAME

CROSS-REFERENCE TO RELATED APPLICATIONS

This application is a divisional application of U.S. application Ser. No. 13/638,370, filed on Dec. 10, 2012, which is a national stage application filed under 35 U.S.C. 371 of International Application No. PCT/KR2011/002206 filed Mar. 31, 2011, which claims priority from Korean Application No. 10-2010-0029233 filed Mar. 31, 2010 and KR 10-2010-0029236 filed Mar. 31, 2010, each of which is incorporated by reference herein in its entirety.

TECHNICAL FIELD

The present invention relates to a one-degree-of-freedom link device and a robot arm using the same. More particularly, the present invention relates to a one-degree-of-freedom link device that can operate regardless of the weight and volume of an actuator, and a robot arm which allows smooth movement of a work section while stably supporting the work section.

BACKGROUND ART

Generally, the operation of a robot or a mechanical apparatus implementing a specific operation is controlled through an actuator directly attached to a joint of an operation implementing part. When driving the mechanical apparatus with the actuator directly attached to the joint of the operation implementing part, the weight and volume of the operation implementing part inevitably increase, thereby making it difficult to achieve a reduction in the size of the mechanical apparatus.

Further, a robot arm of a surgical robot is constructed to perform operations, such as tissue incision or suture, in the body in a limited space. Thus, a robot arm for surgery is limited in size. In a robot arm of a general surgical robot, an actuator is provided to a front end of the robot arm, where joint parts and surgical instruments are mounted, to allow the robot arm to operate at a surgical site. Thus, it is necessary to limit the number of actuators mounted on the robot arm in order to reduce the volume of the robot arm to be inserted into the body. As a result, in order for a general robot arm to move to a position close to tissue to be surgically operated, several sites of the skin 1 are incised and an operation is performed through the incised skin sites, as illustrated in FIG. 1a. Such robot arms $r_1$ and $r_2$ require many skin incisions whose positions are dependent upon the objective of surgery, so that several scars remain on the surgical sites, leaving an unattractive appearance. Particularly, in the case where the surgical sites are likely to be exposed in daily life, unattractive appearance becomes a more serious problem. Additionally, since the actuators increase the weight of the robot arms $r_1$, $r_2$, there is a problem in that a load applied to the robot arms $r_1$, $r_2$ is increased. Moreover, since the robot arms $r_1$, $r_2$ are mounted on different positions, the number of robot arm stands for regulating the positions of the robot arm $r_1$, $r_2$ also increases, and as a result, the installation space becomes small, which makes it difficult to perform a surgical operation.

In view of the above problems, Korean Patent Publication No. 2009-0124552A proposes a robot arm illustrated in FIG. 1b. The robot arm includes a plurality of nodes 20, elastic members 16 connecting the adjacent nodes 20 to constitute joints, and joint driving wires 12, 14 penetrating the nodes 20. Drawing of the joint driving wires 12, 14 leads to contraction or stretching of the elastic members 16 to bend the joints.

In this case, however, since the joint driving wires 12, 14 are connected to each other through the elastic members 16 and the nodes 20, there is a problem that a wire-type drive unit including the joint driving wires 12, 14 is easily damaged when an operation implementing part is replaced with a new one upon operational failure of a mechanical apparatus. Another problem is that the wire-type drive unit has a low strength to allow only an excessively limited load to be applied to an operation part 30. Furthermore, since the joint driving wires 12, 14 control the operation of joint parts of the robot arm as well as a surgical instrument 30, only a limited number of the driving wires 12, 14 can be mounted to control the joints in the robot arm having an extremely limited volume, causing a problem that several sites are incised to allow the robot arm to approach a surgical target, as in existing robot arms. Moreover, a load applied to the robot arm increases with increasing length of the robot arm so that the robot arm undergoes vibration by the load during operation of the surgical instrument 30. This makes it difficult to achieve precise control of the robot arm.

DISCLOSURE

Technical Problem

A first object of the present invention is to provide a one-degree-of-freedom link device in which an output link part is driven by an actuator mounted on an input link part.

A second object of the present invention is to provide a robot driving mechanism, in which a plurality of link devices including a one-degree-of-freedom link device are disposed in a stacking arrangement, that are capable of being driven regardless of the weight and size of an actuator, and can be reduced in size.

A third object of the present invention is to provide a robot arm which has a small volume and an improved ability to drive joints.

A fourth object of the present invention is to provide a surgical robot which includes the robot arm mounted therein, thereby minimizing the incision of a surgery site, reducing the area of installation, and stably controlling the robot arm.

Technical Solution

In order to achieve the first object of the present invention, there is provided a one-degree-of-freedom link device including: a fixed four-node link including four links hingedly joined together, the four links including a fixed link whose position is fixed, a connecting rod positioned at an opposite side of the fixed link, an input-side transmission link connecting the fixed link to one end of the connecting rod, and an output-side transmission link positioned at an opposite side of the input-side transmission link; an input link part hingedly coupled between two ends of the input-side transmission link and having an actuator mounted thereon; and an output link part fixedly coupled to the output-side transmission link to be rotated by the output-side transmission link.

In order to achieve the second object of the present invention, there is provided a two-degree-of-freedom robot driving mechanism including: the one-degree-of-freedom link device; and a two-degree-of-freedom link device coupled to the one-degree-of-freedom link device in a stacking arrangement, and including a four-node link part, an input link part and an output link part, wherein the four-node link part includes four-node links hingedly joined to each another and including a first link, a connecting rod positioned at an opposite side of the first link, an input-side transmission link connecting the first link to one end of the connecting rod, and an output-side transmission link positioned at an opposite side of the input-side transmission link, the four-node link part including a single fixed four-node link in which the first link is a fixed link whose position is fixed, and a single movable four-node link in which the first link is a movable link, the fixed link and the movable link being hingedly joined together, wherein the input link part is hingedly coupled between two ends of the input-side transmission link of the fixed four-node link and has an actuator mounted thereon, wherein the output link part is fixedly coupled to the output-side transmission link of the movable four-node link, wherein a connection joint is coupled between the fixed four-node link and the movable four-node link to transmit driving of the output-side transmission link of the fixed four-node link to the input-side transmission link of the movable four-node link, and wherein an output of the one-degree-of-freedom link device is inputted into the two-degree-of-freedom link device such that all outputs from the two-degree-of-freedom link device are controllable.

In an embodiment, the output link part of the one-degree-of-freedom link device may be fixedly coupled to the movable link of the two-degree-of-freedom link device.

Further, the connection joint may be fixedly coupled to the output-side transmission link of the fixed four-node link and the input-side transmission link of the movable four-node link.

Further, the input link part, the four-node link part and the output link part may be made of a predetermined material.

In order to achieve the second object of the present invention, there is provided an n-degree-of-freedom robot driving mechanism including: the one-degree-of-freedom link device; and n–1 link devices coupled to each other and the one-degree-of-freedom link device in a stacking arrangement, each of the n–1 link devices including a four-node link part, an input link part and an output link part, wherein the four-node link part includes 2 to n four-node links hingedly joined to one another and each including a first link, a connecting rod positioned at an opposite side of the first link, an input-side transmission link connecting the first link to one end of the connecting rod, and an output-side transmission link positioned at an opposite side of the input-side transmission link, the four-node link part including a fixed four-node link in which the first link is a fixed link whose position is fixed and a movable four-node link in which the first link is a movable link moving along a limited path, the first links of the four-node links adjacent to each other being hingedly joined to each other, wherein the input link part is hingedly coupled between two ends of the input-side transmission link of the first four-node link of the four-node link part and has an actuator mounted thereon, wherein the output link part is fixedly coupled to the output-side transmission link of the last four-node link in each four-node link part, wherein outputs of the 1- to (n–1)-degree-of-freedom link devices are inputted into 2- to n-degree-of-freedom link devices, respectively, wherein each of the link devices includes a connection joint coupled between the output-side transmission link and the input-side transmission link of the adjacent four-node links to transmit a driving force between the four-node links, and wherein the first four-node link of the four-node link part is the fixed four-node link, and the other four-node links of the four-node link part are movable four-node links, where n is an integer equal to or greater than 2.

In an embodiment, the connection joint may be fixedly coupled to the output-side transmission link and the input-side transmission link of the adjacent four-node links.

The output link parts of the 1- to (n–1)-degree-of-freedom link devices may be fixedly coupled to the movable links of the last four-node links of the 2- to n-degree-of-freedom link devices, respectively.

The first links positioned in the same order may be joined to one another in a stacking arrangement in the n-degree-of-freedom robot driving mechanism.

The input link part, four-node link part and output link part may be made of a predetermined material.

In order to achieve the third object of the present invention, there is provided a robot arm including: a work section adapted to perform a predetermined operation; a drive section where an actuator adapted to actuate the work section is mounted; and a position control section coupled between the work section and the drive section to transmit a force of the actuator to the work section, wherein a plurality of link devices including four-node links are coupled to each other in a stacking arrangement to perform the predetermined operation of the work section via the actuator, and wherein the four-node links of the link devices are coupled to each other in a stacking arrangement in the position control section.

In an embodiment, each of the link devices may include an input link part disposed in the drive section, a four-node link part including at least one four-node link, and an output link part coupled to a distal end of the four-node link part, wherein the four-node link part includes four links hingedly joined to one another and including a first link, a connecting rod positioned at an opposite side of the first link, an input-side transmission link connecting the first link to one end of the connecting rod, and an output-side transmission link positioned at an opposite side of the input-side transmission link.

The four-node link part may include a single fixed four-node link in which the first link is a fixed link whose position is fixed, and the robot arm may be provided with a one-degree-of-freedom link device including an input link part hingedly coupled between two ends of the input-side transmission link and having an actuator mounted thereon, and an output link part fixedly coupled to the output-side transmission link at a predetermined angle.

The robot arm may include a two-degree-of-freedom stack type link mechanism, which includes the one-degree-of-freedom link device and a two-degree-of-freedom link device coupled to the one-degree-of-freedom link device in a stacking arrangement, wherein the two-degree-of-freedom link device includes a four-node link part including a single fixed four-node link and a single movable four-node link in which the first link is a movable link, an input link part hingedly coupled between two ends of the input-side transmission link of the fixed four-node link and having an actuator mounted thereon, and an output link part fixedly coupled to the output-side transmission link of the movable four-node link and rotated by the output-side transmission link, wherein a connection joint is coupled between the fixed four-node link and the movable four-node link to transmit driving of the output-side transmission link of the fixed four-node link to the input-side transmission link of the movable four-node link, and wherein an output of the one-degree-of-freedom link device is inputted into the two-degree-of-freedom link device such that all outputs of the two-degree-of-freedom link device are controllable.

Preferably, the output link part of the one-degree-of-freedom is fixedly coupled to the movable link of the two-degree-of-freedom link device.

Preferably, the connection joint is fixedly coupled to the output-side transmission link of the fixed four-node link and the input-side transmission link of the movable four-node link.

In a further preferred embodiment, the one-degree-of-freedom link device and n−1 link devices are coupled to each other in a stacking arrangement, wherein each of the n−1 link devices includes a four-node link part having two to n four-node links that include the fixed four-node links and movable four-node links in which first links are movable links, with the adjacent first links hingedly joined to each other, an input link part hingedly coupled between two ends of the input-side transmission link of each of the first four-node links that constitutes the four-node link part and having an actuator mounted thereon, and an output link part fixedly coupled to the output-side transmission link of each of the last four-node links of the four-node link part, wherein the n link devices are coupled to one another in a stacking arrangement such that outputs of the 1- to (n−1)-degree-of-freedom link devices are inputted into 2- to n-degree-of-freedom link devices, respectively, whereby all outputs of the n-degree-of-freedom link device are controllable, wherein a connection joint is coupled between the output-side transmission link and the input-side transmission link of the four-node links adjacent to each other to transmit a driving force between the four-node links, and wherein each of the link devices has an n-degree-of-freedom stack type link mechanism in which the first four-node link of the four-node link part is the fixed four-node link and the other four-node links are the movable four-node links, where n is an integer equal to or greater than 3.

In the n-degree-of-freedom stack type link mechanism, the connection joint may be fixedly coupled to the output-side transmission link and the input-side transmission link of the adjacent four-node links.

In the n-degree-of-freedom stack type link mechanism, the output link parts of the 1- to (n−1)-degree-of-freedom link devices may be fixedly coupled to the movable links of the last four-node links of the 2- to n-degree-of-freedom link devices, respectively.

In the n-degree-of-freedom stack type link mechanism, the first links positioned in the same order may be coupled to one another in a stacking arrangement.

The work section may be made of a predetermined material.

In order to achieve the fourth object of the present invention, there is provided a surgical robot including: a robot driving unit including the robot arm and a robot arm stand adapted to control the position of the robot arm; and a robot console into which an operation command of the robot driving unit is inputted.

In an embodiment, the surgical robot may further include a wire adapted to transmit the operation command inputted from the robot console to the work section, and a guide coupled to the position control section of the robot arm and fixing the installation position of the wire.

Advantageous Effects

According to the present invention, since a plurality of link devices, each including a four-node link as a parallel type link, are hingedly coupled to one another, a robot driving mechanism can easily support a high load, and an actuator and a device adapted to drive the actuator are separated from a joint of the link device. Therefore, the robot driving mechanism can be driven regardless of the weight and size of the actuator and the actuator control device.

In addition, since a position control section can freely control the driving position of a work section when the actuator is simply provided at a position of a drive section, the position and width of an incision site into which the robot arm is inserted can be reduced and it is possible to monitor the surgical situation regardless of the position of the robot arm in the body. Furthermore, since a load of the robot arm is uniformly distributed by a four-node link as a parallel type link of the position control section, it is possible to control the drive of the robot arm in a stable manner, regardless of the weight and volume of the actuator and the actuator control unit. Since the number of wires adapted to control the work section can be minimized, the volume of the robot arm can be reduced. Moreover, since the operational position of the work section can be freely controlled even when a plurality of robot arms are mounted on the same position, it is possible to minimize the area where a robot arm stand is installed.

DESCRIPTION OF DRAWINGS

FIGS. 1a and 1b are front views of a general robot arm;

FIG. 2 is a front view of link devices constituting a robot arm in a coupled state according to an embodiment of the present invention;

FIG. 3 is a front view of the link device constituting a robot arm in a separated state according to the embodiment of the present invention is coupled;

FIG. 4 illustrates front views of robot arms according to embodiments of the present invention;

FIG. 5 is a perspective view of a robot arm according to a further embodiment of the present invention;

FIG. 6 is a partial perspective view of a surgical robot according to an embodiment of the present invention;

FIG. 7 illustrates conceptual diagrams of a one-degree-of-freedom link device mounted on a robot arm according to an embodiment of the present invention;

FIG. 8 illustrates conceptual diagrams for explaining an operation principle of a two-degree-of-freedom stack type link mechanism mounted on a robot arm according to an embodiment of the present invention;

FIG. 9 illustrates conceptual diagrams for explaining an operation principle of an n-degree-of-freedom stack type link mechanism mounted on a robot arm according to a further embodiment of the present invention; and FIG. 10 is a view for explaining the centre of gravity in a robot equipped with a robot arm according to an embodiment of the present invention.

<Explanation of Reference Numerals>

100: One-degree-of-freedom link device,
200: Two-degree-of-freedom link device
110, 210: Input link parts
122, 222: First four-node links
122a, 222a, 224a: Input-side transmission links
122b, 222b, 224b: Connecting rods
122c, 222c, 224c: Output-side transmission links
122d, 222d, 224d: First links -continued <Explanation of Reference Numerals>

| | |
|---|---|
| 130, 230: Output link parts | 223: Connection joint |
| 224: Second four-node link | $J_1$, $J_2$: Fixed joints |
| RA: Robot arm | RS: Robot arm stand |
| 10: Robot arm | 15: Load |
| 20: Body | 25: Power generating unit |
| 33: Wire | 35: Guide |

BEST MODE

The present invention will now be described in detail.

The present invention provides a one-degree-of-freedom link device including: a fixed four-node link in which four links are hingedly joined together in a rectangular shape and include a fixed link whose position is fixed, a connecting rod positioned at an opposite side of the fixed link, an input-side transmission link connecting the fixed link to one end of the connecting rod, and an output-side transmission link positioned at an opposite side of the input-side transmission link; an input link part hingedly coupled between two ends of the input-side transmission link and having an actuator mounted thereon; and an output link part fixedly coupled to the output-side transmission link at a certain angle to be rotated by the output-side transmission link.

Although an n-degree-of-freedom link device generally refers to a link device in which n inputs and n outputs are provided, the n-degree-of-freedom link device of the present invention refers to a link device including n outputs. Herein, any link device including n output despite incomplete control of the degree of freedom is defined as an n-degree-of-freedom link device.

A robot driving mechanism including the one-degree-of-freedom link device has the ability to structurally support a large force because a plurality of link devices including a four-node link as a parallel type link are disposed in a stacking arrangement. That is, since a parallel type link, such as the four-node link, can structurally withstand a large force and the link devices including the parallel type link are coupled to each other in a stacking arrangement, a load applied to the robot driving mechanism is uniformly distributed on the link devices despite an increase in the length of the four-node link part of each of the link devices stacked in the robot driving mechanism. As a result, the robot driving mechanism of the present invention can support a large force.

Since such the robot driving mechanism includes no actuator at its joint while supporting a large force, an operation part of the robot driving mechanism can be reduced in size and weight, thus enabling the use of the robot driving mechanism everywhere. Particularly, the robot driving mechanism can be applied to surgical robots for minimally invasive surgery, etc.

A separate wire or actuator is not provided between the link devices. Thus, the robot driving mechanism of the present invention has an advantage in that the link devices can be easily replaced with new ones during the emergency situation. Due to the structural advantage, the robot driving mechanism of the present invention permits easy replacement of the respective links constituting the link devices as well as the link devices constituting the robot driving mechanism. Therefore, the robot driving mechanism may be constituted by mounting link devices of different materials depending on where it is used. For example, in the case of using the robot driving mechanism of the present invention in a working space where only a local area is at high temperature, the robot driving mechanism does not need to have high heat resistance as a whole, and instead only a portion of the robot driving mechanism that operates at the hot area may be constructed to have heat resistance. Thus, the robot driving mechanism of the present invention can its desired work with no difficulty even when only a four-node link part and an output link part of some link devices constituting the robot driving mechanism are resistant to heat without the need to make all parts of the robot driving mechanism resistant to heat.

The present invention also provides a robot arm including: a work section adapted to perform a specific operation; a drive section including an actuator adapted to actuate the work section; and a position control section coupled between the work section and the drive section to transmit a force of the actuator to the work section, wherein a plurality of link devices including four-node links as parallel type links are joined to each other in a stacking arrangement such that the operation of the work section is performed by the actuator, and wherein the four-node links of the link devices are coupled to each other in a stacking arrangement in the position control section.

The robot arm of the present invention can structurally support a large force since a plurality of link devices including four-node links as parallel type links are coupled to each other in a stacking arrangement, as described above. That is, since a load is distributed over each of the links constituting the four-node link of each of the link devices coupled to each other in a stacking arrangement and a force applied to the work section of the robot arm is uniformly distributed over each of the link devices coupled in a stacking arrangement, the robot arm of the present invention can support a large force, thus eliminating the need to install an actuator in the joint of the robot arm.

The robot arm of the present invention controls a bending angle of the position control section by driving the stack of the link devices to facilitate movement of the work section having a surgery instrument mounted thereon to a surgery site. Thus, the position control section can be stably driven without the need to install an actuator or a wire at each joint of the position control section, unlike the prior art. That is, the robot arm of the present invention may perform its operation with no difficulty after incising only a single surgical site, which minimizes scars. In addition, the robot arm of the present invention can perform a surgical operation efficiently even when an incised site is distant away from a surgery site. A surgical operation can be performed on a site that is not exposed in daily life.

Even when an actuator, a circuit adapted to control the actuator or a wire is provided to the robot arm in order to control the operation of the work section, the position control section can control the operation of the work section using only the plurality of link devices, and thus there is no need for an additional actuator. Thus, in comparison with the prior art, the number of actuators, control circuits, and wires mounted on the position control section of the robot arm according to the present invention can be reduced, enabling reduction in the size and weight of the robot arm to be inserted into a surgical site. In addition, a load on the position control section is actually reduced and a load supported by the robot arm is distributed over the plurality of link devices. This enables stable control over the position of the work section. Further, since each of the link devices includes a four-node link as a parallel type link, a load applied to the link device is distributed over the four-node link, ensuring stable driving of the robot arm according to the present invention.

A robot arm for such a surgical robot may perform minimum invasive surgery (MIS) by means of a thin arm structure and an endoscope. The use of the robot arm allows rapid recovery of patients and enables exact surgery through an optimum surgical site, contributing to an increase in surgery success rate. Under these circumstances, robot-based surgery has attracted attention as a new surgical method satisfying both medical teams and patients. Surgical robots that are currently in use can be broadly classified into robots for celioscopic surgery of soft tissues, such as the prostate, the stomach and the heart, robots for artificial joint surgery of hard tissues, such as the knee joint, robots for blood vessel surgery using catheters, etc.

The use of such surgical robots improves the ability to precisely suture surgical sites without hand tremor and has an improved ability to rotate compared to existing surgical instruments. These advantages enable minimal invasive surgery (MIS).

The present invention will be explained in more detail with reference to the following preferred embodiments. However, it will be obvious to those skilled in the art that these embodiments are provided for more specifically explaining the invention and are not intended to limit the scope of the invention.

FIGS. 2 and 3 illustrate link devices constituting a robot arm according to an embodiment of the present invention.

The robot arm of the present invention is broadly divided into a drive section, a position control section, and a work section, wherein a plurality of link devices are coupled to each other in a stacking arrangement for all of the constituent sections. Each of the link devices includes an input link part positioned in the drive section, a four-node part including one or more four-node links positioned in the position control section, and an output link part coupled to one end of the four-node link part. A portion of the output link part is positioned in the position control section, and the remaining portion thereof is positioned in the work section.

Referring to FIG. 2, the link devices include a one-degree-of-freedom link device 100 and a two-degree-of-freedom link device 200. An output link part 130 of the one-degree-of-freedom link device 100 is positioned in the position control section of the robot arm, and an output link part 230 of the two-degree-of-freedom link device 200 is positioned in the work section of the robot arm.

Due to the structure in which the link devices including four-node links as parallel type links are coupled together in a stacking arrangement, as described above, the robot arm can advantageously endure a large force on the work section despite an increase in the length of the position control section.

The four-node link part of the link device may include at least one four-node link. The four-node link part of the one-degree-of-freedom link device 100 includes a single four-node link 122, and the four-node link part of the two-degree-of-freedom link device 200 includes two four-node links 222, 224.

In a stack type link mechanism to which the link devices are coupled, the output link part 130 of the one-degree-of-freedom link device 100 and the second four-node link 224 of the two-degree-of-freedom link device 200 are integrally coupled to each other. With this structure it is possible to drive the output link part 230 of the two-degree-of-freedom link device 200 whose degree of freedom is 2. Although the two-degree-of-freedom link device 200 has a degree of freedom of 2, only one input value is provided by the input link part 210. Thus, coupling of the one-degree-of-freedom link device 100 and the two-degree-of-freedom link device 200 enables input of an output value of the one-degree-of-freedom link device 100 to the two-degree-of-freedom link device 200, and as a result, two input values are inputted to the two-degree-of-freedom link device 200 whose degree of freedom is two.

The four-node link includes four links hingedly joined to one another via pins, and driving modes of the four-node link vary depending on what link is to be fixed. The four-node link includes an input-side transmission link 122a, 222a or 224a positioned in the input link part 110 or 210, an output-side transmission link 122c, 222c or 224c positioned in the output link part, a connecting rod 122b, 222b or 224b coupled between the input-side transmission link 122a, 222a or 224a and the output-side transmission link 122c, 222c or 224c, and a first link 122, 222d or 224d positioned at an opposite side of the connecting rod 122b, 222b or 224b. The four links constituting the four-node link are hingedly joined together. The four-node link may be classified into a fixed four-node link and a movable four-node link depending on whether the first link is a fixed link or a movable link.

The fixed link of the fixed four-node link 122 or 222 refers to the first link 122d or 222d whose position is fixed, and the movable link of the movable four-node link 224 refers to the first link 224d whose position is not fixed but trajectory is limited by the other link device coupled thereto. That is, since the first link 224d positioned in the second four-node link 224 of the two-degree-of-freedom link device is a movable link, it is not fixed unlike the first links 122d, 222d positioned in the first four-node links 122, 222 of the one-degree-of-freedom link device 100 and the two-degree-of-freedom link device 200. However, the moving trajectory of the first link 224d is limited by the output link part 130. Thus, first four-node links 122, 222 of the one-degree-of-freedom link device 100 and the two-degree-of-freedom link device 200 are fixed four-node links, and the second four-node link 224 of the two-degree-of-freedom link device 200 is a movable four-node link.

Since the output link part 130 or 230 is fixedly coupled to the output-side transmission link 122c or 224c of the four-node link 122 or 224 positioned at one end of each of the four-node link parts, the output link part 130 or 230 is driven through the corresponding four-node link part. To this end, fixed joints J1, J2 are fixedly coupled between the output-side transmission link and the output link part in the link device.

In the four-node links 222, 224, the first links 222d, 224d are hingedly joined together and a connection joint 223 is provided in the position where the first links 222d, 224d are hingedly joined together. With this arrangement, driving of the front four-node link 222 is transmitted to the rear four-node link 224. The connection joint 223 may be hingedly coupled to the output-side transmission link 222d and the input-side transmission link 224a connected to each other or may be fixedly coupled thereto such that the output-side transmission link 222d and the input-side transmission link 224a can be maintained at a certain angle to each other.

This structure may be applied not only to the link devices 100, 200 of the two-degree-of-freedom stack type link mechanism, but also to the link devices of an n-degree-of-freedom stack type link mechanism, which will be described below.

Here, the four-node link may be a locker in which the input-side transmission links 122a, 222a, 224a and the output-side transmission link 122c, 222c, or 224c reciprocate at a certain angle. When the input-side transmission links 122a, 222a, 224a and the output-side transmission link 122c, 222c or 224c are constructed as a locker, the robot driving mechanism can be advantageously driven even in a small space.

FIG. 4 illustrates front views of robot arms operated in the body according to embodiments of the present invention. Specifically, FIGS. 4a and 4b are front views of a plurality of robot arms coupled to the same position, FIGS. 4c and 4d are front views of a plurality of robot arms coupled to different positions. FIG. 5 is a front view of a robot arm having a wire according to a further embodiment of the present invention.

Each robot arm RA is operated in the body by a stack type link mechanism including a plurality of link devices. When the robot arm RA inserted into the body receives a force from a drive section 510 having an actuator mounted thereon, joints are bent and a position control section 520 is deformed, as illustrated in FIGS. 4a and 4b, so that a work section 530 performs a desired operation on a surgical site S. For example, a desired operation is performed by mounting surgical scissors on the work section 530 when incision is needed or by mounting forceps thereon when it is intended to hold a blood vessel. A plurality of robot arms RA may be inserted into the body during surgery. In this case, since the work sections of the robot arms RA may be freely moved through driving of the position control sections 520, the robot arms RA mounted on the same position may easily approach a surgical site after inserted into a single incised site, as illustrated in FIGS. 4a and 4b.

As illustrated in FIGS. 4c and 4d, the separated robot arms RA are coupled to each other. In this case as well, the robot arms RA can control the position control sections 520 such that the work sections 530 move to a position close to the surgical site S, regardless of the angle between the robot arms upon insertion of the robot arms through the incised site.

When the robot arms RA are inserted into the surgical site, it is preferred to reduce the volumes of the robot arms RA, as illustrated in FIG. 4d. After a portion of the skin 1 is minimally incised, the robot arm RA may be inserted with the incised site held by a retractor 550. The shape of the retractor 550 is not limited.

The shape of the robot arm RA according to the present invention may be freely varied without any actuator on the joints of the robot arm RA provided in the position control section 520 as described above. In addition, it is possible to drive the robot arm RA regardless of the weight and size of the actuator because the positions of the joints of the robot arm RA are separated from the actuator and an actuator system for actuating the joints.

The work section 530 of the robot arm RA is coupled to the plurality of link devices disposed in a stacking arrangement. This coupling enables control over the driving of a surgical instrument mounted on the work section 530. In order to control the work section 530 with more precision, the robot arm may further include an actuator adapted to control driving of the work section 530 or a wire (w) adapted to transmit an electrical signal to the actuator. That is, the robot arm RA may have a space in which the wire (w) is mounted, as illustrated in FIG. 5. To this end, the robot arm RA may have guides (g) arranged at regular intervals to hold the position of the wire (w). Each of the guides (g) may have holes through which the wire (w) passes, as illustrated in FIG. 5. Alternatively, the first link of the link device constituting the robot arm may be formed in the shape of a tube to perform a role as a guide. Here, since the wire (w) controls only the driving of the surgical instrument mounted on the work section 530, an increase in the volume of the robot can be limited as low as possible.

In the work section 530, an output link part of the link device may act as a surgical instrument. Alternatively, a surgical instrument may be mounted in the work section 530. In this case, the surgical instrument operates through the output link part of the link device. Alternatively, a surgical instrument may be coupled to the output link part. In this case, the surgical instrument may be driven by a control command transmitted through the wire (w).

Here, the work section 530 of the robot arm RA may be made of a radiation transmitting material to confirm whether a surgery is well performed. For example, when the robot arm RA is inserted into the body to perform a surgical operation, radiation, such as α-ray, β-ray, γ-ray, x-ray or neutron ray, may be irradiated to confirm whether the surgery is efficiently performed by the robot arm RA or whether the surgery is properly completed. When the work section 530 or the robot arm RA is made of a material through which radiation can transmit, it is possible to monitor the surgical procedure by securing a clear view without retracting the robot arm RA from the body. Thus, the work section 530 of the robot arm or the robot arm RA are preferably made of a radiation transmitting material, such as a polymer material (e.g., a plastic material) or a ceramic material. Optionally, a surgical instrument to be positioned in the work section 530 may be made of a radiation transmitting material.

FIG. 6 is a schematic view of a surgical robot according to an embodiment of the present invention.

The robot arm RA of the present invention is mounted on a surgical robot, as illustrated in FIG. 6. The surgical robot of the present invention includes a robot driving unit including the robot arm RA, and a robot arm stand RS adapted to control the position of the robot arm RA such that the robot arm RA is moved to a surgical site; and a robot console RC to which operation commands of the robot driving unit are inputted. The robot arm RA may be provided with a camera to photograph a site into which the robot arm RA is inserted.

FIG. 6 illustrates a single robot arm RA mounted on the robot arm stand RS for ease of explanation of the relationship between the robot arm stand RS and the robot arm RA. However, it should be understood that a plurality of robot arms RA may be mounted on the robot arm stand RS because the position of the work section may be easily changed by the position control section. The position and angle of a conventional robot arm inserted into the body are limited. In contrast, according to the present invention, a plurality of robot arms RA may be mounted on a single robot arm stand RS. Even in this case, the work section can be easily moved to a surgical site. As such, only a single robot arm stand can be installed in an operating room to efficiently perform a surgical operation. That is, the surgical robot of the present invention requires a smaller area for installation and provides a larger available space in an operating room to perform surgery in a more efficient manner than a conventional surgical robot.

Next, a description will be given regarding a method for performing a surgical operation using the surgical robot of the present invention. After anaesthesia of a patient on a bed, the robot arm RA of the present invention is inserted into the abdominal cavity of the patient by controlling the length of the robot arm stand RS or properly rotating the robot arm stand. When the robot arm RA is placed at a predetermined insertion position, a surgical operation is performed while controlling the shape of the robot arm RA through the robot console RC.

Next, the operational principle of the robot arm according to the present invention will be described in more detail.

FIG. 7 illustrates conceptual diagrams of a one-degree-of-freedom link device used in a robot arm according to an embodiment of the present invention.

The robot arm of the present invention includes a stack type link mechanism having a multiple degree of freedom. Before describing the robot arm of the present invention, the terms and mathematical symbols used herein are described with reference to the one-degree-of-freedom link device.

FIG. 7a represents an input link part of the one-degree-of-freedom link device illustrated in FIG. 3. In FIG. 7a, $L_{O2}$ denotes the length of the second link of the input link part. This can be generalized as follows: an arbitrary constant $L_{jk}$ and an arbitrary variable $\theta_{jk}$ denote the $k^{th}$ link and the $k^{th}$ joint of the $j^{th}$ four-node link part in the input link part, respectively. For mechanical analysis, coordinates (X, Y) and a direction angle $\Phi$ of a middle point of $L_{O3}$ designated as a target point $P_0$ may be expressed by Loop 1 below:

$$\begin{cases} X_{OP} = L_{01} + L_{02}\cos(\theta_{01}) + \dfrac{L_{03}}{2}\cos(\theta_{01} + \theta_{02}) \\ Y_{OP} = L_{02}\sin(\theta_{01}) + \dfrac{L_{03}}{2}\sin(\theta_{01} + \theta_{02}) \\ \Phi_{OP} = \theta_{01} + \theta_{02} \end{cases} \quad (1)$$

Further, the target point $P_0$ of FIG. 6a may be expressed by Loop 2 below:

$$\begin{cases} X_{OP} = X_{03} + \dfrac{L_{03}}{2}\cos(\theta_{03}) \\ Y_{OP} = \dfrac{L_{03}}{2}\sin(\theta_{03}) \\ \Phi_{OP} = \theta_{03} + \pi \end{cases} \quad (2)$$

Expressions 1 and 2 represent the theory of mechanics for the same point through different ways. Expressions 1 and 2 can be differentiated with respect to time as follows.

$$\begin{bmatrix} \dot{X}_{OP} \\ \dot{Y}_{OP} \\ \dot{\Phi}_{OP} \end{bmatrix} = \begin{bmatrix} 1 & -L_{02}S_{\theta_{01}} - \dfrac{L_{03}}{2}S_{\theta_{01}+\theta_{02}} & -\dfrac{L_{03}}{2}S_{\theta_{01}+\theta_{02}} \\ 0 & L_{02}C_{\theta_{01}} + \dfrac{L_{03}}{2}C_{\theta_{01}+\theta_{02}} & \dfrac{L_{03}}{2}C_{\theta_{01}+\theta_{02}} \\ 0 & 1 & 1 \end{bmatrix} \begin{bmatrix} \dot{L}_{01} \\ \dot{\theta}_{01} \\ \dot{\theta}_{02} \end{bmatrix} \quad (3)$$

$$\begin{bmatrix} \dot{X}_{OP} \\ \dot{Y}_{OP} \\ \dot{\Phi}_{OP} \end{bmatrix} = \begin{bmatrix} -\dfrac{L_{03}}{2}S_{\theta_{03}} \\ \dfrac{L_{03}}{2}C_{\theta_{03}} \\ 1 \end{bmatrix} [\dot{\theta}_{03}] \quad (4)$$

Since Expressions 3 and 4 represent velocity at the same point, they can be simplified as follows.

$$[[A_o]_1; \ [A_o]_2; \ [A_o]_3;] \begin{bmatrix} \dot{L}_{01} \\ \dot{\theta}_{01} \\ \dot{\theta}_{02} \end{bmatrix} = [B_0][\dot{\theta}_{03}] \quad (5)$$

$[A_o]_1;$ $[A_o]_2;$ $[A_o]_3;$ denote the first, second and third column vectors of the 3×3 matrix of Expression 3, respectively. Since the mobility of an input link part <0> is 1, when any one of four joints including translation motion joints and rotation motion joints is set as an input joint, motions and angles of the other three joints are determined. Here, the joint providing an input joint is defined as active joint, and the other joints are defined as passive joints. Arrangement of Expression 5 to place the active joint in the right side and the passive joints in the left side gives:

$$[[A_o]_2; \ [A_o]_3; \ -[B_o]] \begin{bmatrix} \dot{\theta}_{01} \\ \dot{\theta}_{02} \\ \dot{\theta}_{03} \end{bmatrix} = [-[A_0]_{1;}][\dot{L}_{01}] \quad (6)$$

where $L_{01}$ is set as the active joint.

Assuming that there is no singular point in Expression 6, Expression 6 can be converted into:

$$\begin{bmatrix} \dot{\theta}_{01} \\ \dot{\theta}_{02} \\ \dot{\theta}_{03} \end{bmatrix} = [Q_0][\dot{L}_{01}] \quad (7)$$

wherein $[Q_0]=[[A_0]_{2;} \ [A_0]_{3;} -[B_0]]^{-1}[-[A_0]_{1;}]$.

It is possible to obtain a velocity related expression from the input active joint to the passive joints using Expression 7. From Expression 7, a velocity related expression of output $\theta_{03}$ and input $L_{01}$ in FIG. 7a can be obtained as follows:

$$[\dot{\theta}_{03}]=[Q_{0(3,1)}][\dot{L}_{01}] \quad (8)$$

where $[Q_{0(3,1)}]$ means the third component of the row vector $[Q_0]$.

Expression 8 can be generalized as follows:

$$[\dot{\theta}_{0,out}]=[\dot{\theta}_{03}]=[G_0][\dot{U}] \quad (9)$$

wherein $[G_0]$ is a velocity related expression of the output with respect to the input in the input link part, and $\dot{\theta}_{0,out}$ is the final output of the input link part. For example, when a worm gear is positioned in the input link part, the velocity of the output to the input is expressed by a gear ratio below:

$$[G_0]=[r_0] \quad (10)$$

wherein $r_0$ denotes a gear ratio of the worm gear. The link device used in the robot arm of the present invention can obtain a velocity related expression of the input link part, like Expressions 9 and 10, with respect to various input methods.

FIG. 7b illustrates a four-node link <1> and an output link part <fix>. A general four-node link includes four joints and four links, each having a fixed length. However, when the robot driving mechanism is extended to a multiple degree of freedom, the angle of a first link $L_{14}$ may be varied, which are defined as five variables. In the same method as in the mechanical analysis for the input link part of Expressions 1 to 9, a velocity related expression of a passive joint with respect to an active joint in the four-node link can be obtained as follows:

$$\begin{bmatrix} \dot{\theta}_{12} \\ \dot{\theta}_{13} \\ \dot{\theta}_{14} \end{bmatrix} = [Q_1]\begin{bmatrix} \dot{\theta}_{11} \\ \dot{\theta}_{15} \end{bmatrix} \quad (11)$$

wherein $$[Q_1] = \begin{bmatrix} Q_{1(1,1)} & Q_{1(1,2)} \\ Q_{1(2,1)} & Q_{1(2,2)} \\ Q_{1(3,1)} & Q_{1(3,2)} \end{bmatrix},$$

$\dot{\theta}_{11}$ is an active joint as an input joint of the four-node link, and $\dot{\theta}_{15}$ is an angle between the first link $L_{14}$ and the reference axis and is a virtual active joint. That is, $\theta_{15}$ is a passive joint but is defined as an active joint for mechanical analysis. An expression of output with respect to input in the four-node link is:

$$[\dot{\theta}_{14}] = [Q_{1(3,1)} \quad Q_{1(3,2)}] \begin{bmatrix} \dot{\theta}_{11} \\ \dot{\theta}_{15} \end{bmatrix} \quad (12)$$

If the first link L14 is a fixed link fixed to the ground, Expression 12 can be simplified as follows:

$$[\dot{\theta}_{14}] = [Q_{1(3,1)}][\dot{\theta}_{11}] \quad (13)$$
$$= [G_1][\dot{\theta}_{11}]$$

When the one-degree-of-freedom link device is compared with the four-node link <1> illustrated in FIG. 7b, the following relations can be obtained:

$$\begin{Bmatrix} \theta_{11} = \theta_{0,out} \\ \dot{\theta}_{11} = \dot{\theta}_{0,out} \end{Bmatrix} \quad (14)$$

$$\begin{Bmatrix} \phi_1 = \theta_{1out} = \theta_{14} - \theta_{1,fix} \\ \dot{\phi}_1 = \dot{\theta}_{1out} = \dot{\theta}_{14} \end{Bmatrix} \quad (15)$$

When the input link part <0>, the first four-node link <1> and the output link part <fix> fixed to the four-node link are combined using the relationship between Expressions 14 and 15, a velocity related expression of output $\dot{\phi}_1$ with respect to input $\dot{\theta}_{11}$ of the first four-node link <1> can be obtained as follows:

$$[\dot{\phi}_1] = [G_1][\dot{\theta}_{11}] \quad (16)$$

When Expression 16 is arranged into an expression related to input U using Expression 9, the following expression is obtained:

$$[\dot{\phi}_1] = [G_1][G_0][\dot{U}] \quad (17)$$

where $[G_0]$ is an expression related to the input link part, as described in Expression 9, and $[G_1]$ is a velocity related expression of input and output of a one-degree-of-freedom including a single four-node link. Therefore, the velocity related expression of output $\dot{\phi}_1$ with respect to input $\dot{U}$ of the one-degree-of-freedom link device, such as Expression 17, can be obtained.

The stack type link mechanism constituting the robot arm according to the present invention has various degrees of freedom.

Next, a description will be given regarding an expression capable of determining how a four-node link positioned at a distal end of the four-node link part is driven with respect to the input of the first four-node link of the link mechanism.

The robot arm of the present invention constitutes a multiple-degree-of-freedom stack type link mechanism by joining a plurality of link devices. In the multiple-degree-of-freedom stack type link mechanism, the plurality of link devices having a single input and one or more outputs are sequentially joined to one another, wherein the sum of inputs of the plurality of link devices combined with one another is identical to the number of outputs of a link device having the largest output number.

First, a description will be given regarding a method for joining link devices of a two-degree-of-freedom stack type link mechanism as in a robot arm according to an embodiment of the present invention.

FIG. 8 illustrates schematic views of a two-degree-of-freedom stack type link mechanism that constitutes the robot arm of the present invention.

In the robot driving mechanism, a one-degree-of-freedom link device $DOF_1$ having one output and a two-degree-of-freedom link device $DOF_2$ having two outputs are coupled to each other. An output of an output link part $_1L_{1,out}$ of the one-degree-of-freedom link device $DOF_1$ may be inputted into the two-degree-of-freedom link device $DOF_1$ such that all outputs of the two-degree-of-freedom link device $DOF_2$ can be controlled. It can be seen that the four-node link part of the one-degree-of-freedom link device $DOF_1$ includes one four-node link <1, 1> and the four-node link part of the two-degree-of-freedom link device $DOF_2$ includes two four-node links <2, 1>, <2, 2>. Particularly, the output link part $_1L_{1,out}$ of the one-degree-of-freedom link device $DOF_1$ is integrally fixedly coupled to a first link $_2L_{24}$ as a movable link of the movable four-node link <2, 2> positioned at the second position from the input link part <2, 0> of the two-degree-of-freedom link device $DOF_2$.

FIG. 8 specifically illustrates the link devices of the stack type link mechanism as illustrated in FIG. 3. The link devices are coupled to each other in a stacking arrangement. The one-degree-of-freedom link device $DOF_1$ refers to a link device having a single four-node link and the two-degree-of-freedom link device $DOF_2$ refers to a link device having two four-node links. The two-degree-of-freedom stack type link mechanism holds the output link part $_1L_{1,out}$ of the one-degree-of-freedom link device $DOF_1$ and the first link $_2L_{24}$ as a movable link of the two-degree-of-freedom link device $DOF_2$ such that their positions and direction angles are always identical to each other. The first link $_1L_{14}$ as a fixed link of the first four-node link <1, 1> of the one-degree-of-freedom link device $DOF_1$ is always fixed to the ground, which can be thus expressed as follows:

$$\dot{\phi}_1 = [_1\dot{\theta}_{14}] = [_1Q_{1(3,1)}][_1\dot{\theta}_{11}] \quad (18)$$

where <1, 1> denotes the first four-node link of the one-degree-of-freedom link device $DOF_1$, that is, the first four-node link of the link device whose degree of freedom is 1. When this expression is generalized, <i, j> denotes a $j^{th}$ four-node link of an i-degree-of-freedom link device, and $_i\theta_{jk}$ and $_iL_{jk}$ denote the $k^{th}$ joint and the $k^{th}$ link of the $j^{th}$ four-node link of the i-degree-of-freedom link device, respectively. FIG. 8b illustrates the two-degree-of-freedom link device $DOF_2$. Since the first link $_2L_{24}$ as a movable link of <2, 2> is a four-node link that is not fixed to the ground, a relation of output $_2\dot{\theta}_{24}$ with respect to input $_2\dot{\theta}_{21}$ can be obtained as follows:

$$[\dot{\phi}_2] = [_2\dot{\theta}_{24}] = [_2Q_{2(3,1)} \quad _2Q_{2(3,2)}] \begin{bmatrix} _2\dot{\theta}_{21} \\ _2\dot{\theta}_{25} \end{bmatrix} \quad (19)$$

where $_2\dot{\theta}_{25}$ is a virtual active joint as a virtual input of the two-degree-of-freedom link device D0F$_2$ illustrated in FIG. 8$b$.

The first link $_2L_{14}$ as a fixed link of <2, 1> is fixed, which can be thus expressed from Expression 13 as follows:

$$[_2\dot{\theta}_{14}] = [_2Q_{1(3,1)}][_2\dot{\theta}_{11}] \quad (20)$$

From FIG. 8$b$, the following relation can be obtained:

$$_2\theta_{21} = _2\theta_{14} - _2\theta_{1,fix} \quad (21)$$

An output of the first four-node link <2, 1> of the two-degree-of-freedom link device D0F$_2$ functions as an input of the second four-node link <2, 2>. Therefore, arrangement of Expression 21 gives the following velocity related expression:

$$_2\dot{\theta}_{21} = _2\dot{\theta}_{14} \quad (22)$$

Using the relation of Expression 22 and Expression 20, Expression 19 can be arranged as follows:

$$[\dot{\phi}_2] = [_2\dot{\theta}_{24}] \quad (23)$$

$$= [\,_2Q_{2(3,2)} \quad _2Q_{2(3,1)}\,] \begin{bmatrix} _2\dot{\theta}_{25} \\ _2\dot{\theta}_{21} \end{bmatrix}$$

$$= [\,_2Q_{2(3,2)} \quad _2Q_{2(3,1)}\,] \begin{bmatrix} 1 & 0 \\ 0 & _2Q_{1(3,1)} \end{bmatrix} \begin{bmatrix} _2\dot{\theta}_{25} \\ _2\dot{\theta}_{11} \end{bmatrix}$$

As can be seen from Expression 23, the two-degree-of-freedom link device D0F$_2$ of FIG. 8$b$ is defined as a system having two input variables and one output variable. That is, $_2\dot{\theta}_{25}$ is a virtual active joint. This means that the angles of $_2\theta_{25}$ and $\Phi_2$ may be varied by input $_2\dot{\theta}_{11}$. Since this system lacks one degree of freedom having one input and two outputs, the following constraints are considered.

In the one-degree-of-freedom link device D0F$_1$ and the two-degree-of-freedom link device D0F$_2$, the first link $_1L_{14}$ of the one-degree-of-freedom link device D0F$_1$ and the first link $_2L_{14}$ of the two-degree-of-freedom link device D0F$_2$ as fixed links, and the output link device $_1L_{1,out}$ of the one-degree-of-freedom link device D0F$_1$ and the first link $_2L_{24}$ of the two-degree-of-freedom link device D0F$_2$ are coupled to one another, as can be seen from FIG. 8. In other word, since an output $_1\theta_{1,out}$ of the one-degree-of-freedom link device D0F$_1$ is the same as $_2\theta_{25}$ of the second four-node link of the two-degree-of-freedom link device D0F$_2$, the following expression can be obtained:

$$\phi_1 = _1\theta_{1,out} = _1\theta_{14} - _1\theta_{1,fix} = _2\theta_{25} \quad (24)$$

Using the relation of Expression 24, Expression 18, a relationship of the one-degree-of-freedom link device D0F$_1$, and Expression 23, a relationship of the two-degree-of-freedom link device D0F$_2$, can be arranged as follows:

$$\begin{bmatrix} \dot{\phi}_1 \\ \dot{\phi}_2 \end{bmatrix} = \begin{bmatrix} 1 & 0 \\ _2Q_{2(3,2)} & _2Q_{2(3,1)} \end{bmatrix} \begin{bmatrix} _1Q_{(3,1)} & 0 \\ 0 & _2Q_{1(3,1)} \end{bmatrix} \begin{bmatrix} _1\dot{\theta}_{11} \\ _2\dot{\theta}_{11} \end{bmatrix} \quad (25)$$

This can be simply expressed as follows:

$$\begin{bmatrix} \dot{\phi}_1 \\ \dot{\phi}_2 \end{bmatrix} = [G_2] \begin{bmatrix} _1\dot{\theta}_{11} \\ _2\dot{\theta}_{11} \end{bmatrix} \quad (26)$$

Expression 26 is a velocity related expression of output with respect to input of the robot driving mechanism including the one-degree-of-freedom link device D0F$_1$ and the two-degree-of-freedom link device D0F$_2$, as illustrated in FIG. 8. Expression 26 is a relationship having two input variables and two output variables. From Expression 26, it can be seen that the combined system of the two-degree-of-freedom link device D0F$_2$ including two four-node links and the one-degree-of-freedom link device D0F$_1$ including a single four-node link is a two-degree-of-freedom system that can operate like a serial type manipulator.

When the input link parts <1, 0>, <2, 0> are applied to inputs of the first four-node links <1, 1>, <2, 1>, which are planar, respectively, the following expression is obtained:

$$\begin{bmatrix} \dot{\phi}_1 \\ \dot{\phi}_2 \end{bmatrix} = [G_2] \begin{bmatrix} _1G_0 & 0 \\ 0 & _2G_0 \end{bmatrix} \begin{bmatrix} _1\dot{U} \\ _2\dot{U} \end{bmatrix} \quad (27)$$

where $_iG_0$ and $_i\dot{U}$ denote a relationship of output with respect to input of an i-degree-of-freedom link device input link part <i,0> and an input of the i-degree-of-freedom link device, respectively. Therefore, it is possible to obtain a velocity related expression of the two-degree-of-freedom stack type link mechanism like Expression 27. Expression 23 is a link device that lacks one degree of freedom because $_2\theta_{25}$ of the two-degree-of-freedom link device D0F$_2$ mentioned above is actually a virtual active joint as a passive joint. However, when a one-degree-of-freedom link device D0F$_1$ is stacked on the link device of Expression 23, the deficient one degree of freedom is supplemented with the output $\Phi_1$ of the one-degree-of-freedom link device D0F$_1$ to constitute a complete two-degree-of-freedom stack type link mechanism.

Hereinafter, an n-degree-of-freedom stack type link mechanism will be described in detail.

FIG. 9 illustrates schematic views for explaining a coupling method of an n-degree-of-freedom stack type link mechanism constituting the robot arm of the present invention.

In the n-degree-of-freedom stack type link mechanism applied to the robot arm of the present invention, link devices having degrees of freedom of from 1 to n are coupled to each other in a stacking arrangement. In order to make all outputs of the n-degree-of-freedom link device D0F$_n$ controllable, outputs of the 1- to (n−1)-degree-of-freedom link devices are inputted into the 2- to n-degree-of-freedom link devices. Here, n is an integer equal to or greater than 3.

When n is 3, the stack type link mechanism is constituted such that outputs of the one-degree-of-freedom link device D0F$_1$ and the two-degree-of-freedom link device D0F$_2$ are inputted into the two-degree-of-freedom link device D0F$_2$ and the three-degree-of-freedom link device D0F$_3$, respectively. The four-node link part of the (n−1)-degree-of-freedom link device D0F$_{n-1}$ is provided with n−1 four-node links including <n−1, 1> to <n−1, n−1>, and the four-node link part of the n-degree-of-freedom link device D0F$_n$ is provided with n four-node links including <n, 1> to <n, n>. In order to constitute the stack type link mechanism as a complete multiple-degree-of-freedom stack type link mechanism, the output link parts of the 1- to (n−1)-degree-of-freedom link devices are preferably fixedly coupled to the corresponding last four-node links of the four-node link parts of the 2- to n-degree-of-freedom link devices. Particularly, as in the two-degree-of-freedom stack type link mechanism, output link parts $_1L_{1,out}, _2L_{2,out}, _3L_{3,out}, \ldots _{n-1}L_{n-1,out}$ of the 1- to (n−1)-degree-of-freedom link devices are integrally coupled to movable links $_2L_{24}, _3L_{34}, \ldots _nL_{n4}$ of the last four-node links of the 2- to n-degree-of-freedom link devices, respectively. That is, an output link part $_{n-1}L_{n-1,out}$ of the (n−1)-degree-of-freedom link device $D0F_{n-1}$ is integrally coupled to a movable link $_nL_{n4}$ of the $n^{th}$ four-node link of the (n−1)-degree-of-freedom link device, an output link part of the (n−2)-degree-of-freedom link device is integrally coupled to a movable link $_{n-1}L_{n-1,4}$ of the (n−1)$^{th}$ four-node link of the (n−1)-degree-of-freedom link device $D0F_{n-1}$, and an output link part of the (n−3)-degree-of-freedom link device is integrally coupled to a movable link of the (n−2)$^{th}$ four-node link of the (n−2)-degree-of-freedom link device. In the same manner as above, output link parts and movable links of the other link devices are also integrally coupled to one another.

When the multiple-degree-of-freedom link devices are coupled in a stacking arrangement, the first links of the four-node links positioned in the same order are preferably integrally coupled to each other. That is, as illustrated in FIG. 9, it is desirable that the first links of the four-node links indicated by the same hatching are coupled to each other in a stacking arrangement.

In each of the multiple-degree-of-freedom link devices, the first links of the adjacent four-node links are hingedly joined to each other and the first links form a connection joint at the hingedly coupled position, so that driving of a front output-side transmission link is transmitted to a rear input-side transmission link. FIG. 9 illustrates that the four-node links having the first links hingedly joined to each other are formed so as to share portions of the output-side transmission link and the input-side transmission link. Thus, the link devices may be formed to obtain the same effect as that of the structure in which the connection joint is fixedly coupled to the output-side transmission link and the input-side transmission link of the adjacent four-node links.

The first links of the first four-node links in the 1 to n-degree-of-freedom link devices may be fixed links. Only the first link of the one-degree-of-freedom link device is a fixed link. The movable first links of the 2- to n-degree-of-freedom link devices may be stacked and coupled to each other in such a manner that they are fixedly coupled to the fixed link.

Using the relationship of the two-degree-of-freedom stack type link mechanism, a relationship of output with respect to input of the multiple-degree-of-freedom stack type link mechanism can be obtained. By repeating the procedure of Expressions 18 to 26, the following relationship between input velocity and output velocity of an n-degree-of-freedom can be obtained:

$$\begin{bmatrix} \dot{\phi}_1 \\ \dot{\phi}_2 \\ \vdots \\ \dot{\phi}_3 \end{bmatrix} = [G_n] \begin{bmatrix} _1\dot{\theta}_{11} \\ _2\dot{\theta}_{11} \\ \vdots \\ _n\dot{\theta}_{11} \end{bmatrix} \qquad (28)$$

where $[G_n]$ is a velocity related expression of an angle $\dot{\phi}_n$ of each of n output link parts of the n-degree-of-freedom stack type link mechanism and an angle $_n\dot{\theta}_1$ between the input-side transmission link of each of the first four-node links of the 1- to (n−1)-degree-of-freedom link devices and an extension line of an input link part thereof.

A velocity related expression of output with respect to input in the n-degree-of-freedom stack type link mechanism is expressed by:

$$\begin{bmatrix} \dot{\phi}_1 \\ \dot{\phi}_2 \\ \vdots \\ \dot{\phi}_n \end{bmatrix} = [G_n] \begin{bmatrix} _1G_0 & & & \\ & _2G_0 & & \\ & & \ddots & \\ & & & _nG_0 \end{bmatrix} \begin{bmatrix} _1\dot{U} \\ _2\dot{U} \\ \vdots \\ _n\dot{U} \end{bmatrix} \qquad (29)$$

By the above method, it is possible to obtain a general velocity related expression of a robot arm including the stack type link mechanism whose degree of freedom is n.

The input link part, four-node link part and output link part constituting the two-degree-of-freedom robot driving mechanism or an n-degree-of-freedom robot driving mechanism can be easily replaced with new ones. Due to this structural advantage, some or all portions of the link devices constituting the two-degree-of-freedom robot driving mechanism or the n-degree-of-freedom robot driving mechanism can be made of a special material, such as a radiation transmitting material, so that it is possible to confirm whether driving of the robot driving mechanism is suitably performed depending on the desired purpose. Since parts such as a motor, sensors and wires are not used in some or all portions of the robot driving mechanism that actually performs a work, the robot driving mechanism made of such a special material can be driven. For example, when the robot driving mechanism is inserted into a certain space in the industrial field and performs its work, radiation, such as α-ray, β-ray, γ-ray, x-ray or neutron-ray, may be irradiated to confirm whether the work is efficiently performed by the robot driving mechanism. That is, when the robot driving mechanism is made of a radiation transmitting material, a user can perform a desired work using the robot driving mechanism without view obstruction by the robot driving mechanism. Thus, the input link part, four-node link part and output link part constituting the two-degree-of-freedom robot driving mechanism or the n-degree-of-freedom robot driving mechanism are preferably made of a radiation transmitting material, such as a polymer material (e.g., a plastic material) or a ceramic material. It should be understood that various materials may also be used according to working conditions.

A conventional movable robot has a structure in which a motor is directly mounted on a joint of a robot arm of a robot body to lift a load. In this case, the center of gravity of the robot is placed on the robot arm rather than on the robot body. When the center of gravity is placed outside the movable robot, the robot cannot stably support a load applied to the robot arm and is likely to fall. To prevent the likelihood of falling, it is necessary to excessively increase the size and weight of the movable robot than is necessary according to the work area of the robot arm and the load applied to the robot arm.

In contrast, when the robot arm based on the stacking mechanism according to the embodiments of the present invention is used, a motor adapted to drive the robot arm is placed within the body of the movable robot. That is, the position of the motor can be arbitrarily selected without the need to attach the motor to the joint of the robot arm. This selection enables the adjustment of the center of gravity of the robot to an arbitrary position inside the robot body.

FIG. 10 illustrates where the center of gravity 50 is placed in a robot including a robot arm 10 according to an embodiment of the present invention. In FIG. 10, the robot including the robot arm 10 may include a body 20 including a power generator 25 (for example, a motor), and a power transmitting unit connected between the robot arm 10 and the body 20 to transmit power to the robot arm. The power transmitting unit may include a wire 33 adapted to transmit a specific operation to the work section of the robot arm using the generated power, and a guide 35 coupled to the position control section of the robot arm to hold the position of the wire. Due to this construction, the center of gravity 50 is placed inside the robot body 20, which guarantees stable operation of the movable robot and a relatively large working area of the robot arm and enables an operation of lifting a heavy load. It can be seen from FIG. 10 that while the movable robot supports a large load 15 using the robot arm 10, the center of gravity 50 is still placed inside the body 50, which allows the robot to stably perform a work. A person having ordinary knowledge in the art would suitably adjust the connection and positions of the power generator 25 and the power transmitting units 33, 35 depending on the situations of the embodiments of the present invention in order to determine the position of the center of gravity 50.

The robot arms according to the embodiments of the present invention and the robots using the robot arms may be applied to underwater robots, the center of gravity of which is considered important. In this case, since precision parts, such as a motor and a sensor, are not mounted to the robot arm, only the body and the interior of the robot are waterproofed. As described above, the stacking mechanisms according to the embodiments of the present invention can be provided to underwater robots or flying robots, whose bodies cannot be fixed to the ground, and can be used in a variety of applications.

Those skilled in the art will readily recognize and appreciate that simple modifications and variations of the invention can be made and such modifications and variations are encompassed within the scope of the invention.

The invention claimed is:

1. An n-degree-of-freedom robot driving mechanism, comprising:
   a one-degree-of-freedom link device; and
   n−1 link devices coupled to each other and to the one-degree-of-freedom link device in a stacking arrangement, each of the n−1 link devices comprising a four-node link part, an input link part, and an output link part,
   wherein the four-node link part comprises 2 to n four-node links hingedly joined to one another and each comprising a first link, a connecting rod positioned at an opposite side of the first link, an input-side transmission link connecting the first link to one end of the connecting rod, and an output-side transmission link positioned at an opposite side of the input-side transmission link, the four-node link part comprising a fixed four-node link in which the first link is a fixed link whose position is fixed and a movable four-node link in which the first link is a movable link moving along a limited path, the first links of the four-node links adjacent to each other being hingedly joined to each other,
   wherein the input link part is hingedly coupled between two ends of the input-side transmission link of the first four-node link of the four-node link part and has an actuator mounted thereon,
   wherein the output link part is fixedly coupled to the output-side transmission link of the last four-node link in each four-node link part,
   wherein outputs of the 1- to (n−1)-degree-of-freedom link devices are inputted into 2- to n-degree-of-freedom link devices, respectively,
   wherein each of the link devices comprises a connection joint coupled between the output-side transmission link and the input-side transmission link of the adjacent four-node links to transmit a driving force between the four-node links, and
   wherein the first four-node link of the four-node link part is the fixed four-node link, and the other four-node links of the four-node link part are movable four-node links, where n is an integer equal to or greater than 3,
   wherein the one-degree-of-freedom link device comprises a four-node link comprising four links hingedly joined together, the four links comprising a base link, a connecting rod positioned at an opposite side of the base link, an input-side transmission link connecting the base link to one end of the connecting rod, and an output-side transmission link positioned at an opposite side of the input-side transmission link; and
   an output link part fixedly coupled to the output-side transmission link to be rotated by the output-side transmission link,
   wherein in a case that external force is applied to the input-side transmission link, the external force is transmitted to the output link part via the four-node link.

2. The apparatus according to claim 1, wherein the connection joint is fixedly coupled to the output-side transmission link and the input-side transmission link of the adjacent four-node links.

3. The apparatus according to claim 1, wherein the output link parts of the 1- to (n−1)-degree-of-freedom link devices are fixedly coupled to the movable links of the last four-node links of the 2- to n-degree-of-freedom link devices, respectively.

4. The apparatus according to claim 1, wherein the first links positioned in the same order are joined to one another in a stacking arrangement in the n-degree-of-freedom robot driving mechanism.

5. The apparatus according to claim 1, wherein the input link part, four-node link part and output link part are made of a predetermined material.

6. A link device, comprising:
   a 1st position control section comprising 1st four links hingedly joined together and 1st output link; and
   a 2nd position control section comprising 2-1st four links hingedly joined together and 2-2nd four links hingedly joined together;
   wherein the 1st four links comprising a 1st base link, a 1st connecting rod positioned at an opposite side of the 1st base link, an 1st input-side transmission link connecting the 1st base link to one end of the 1st connecting rod, an 1st output-side transmission link positioned at an opposite side of the 1st input-side transmission link and the 1st output link coupled to the output-side transmission link to be rotated by the 1st output-side transmission link,
   wherein the 2-1st four links comprising a 2-1st base link, a 2-1st connecting rod positioned at an opposite side of the 2-1st base link, an 2-1st input-side transmission link connecting the 2-1st base link to one end of the 2-1st connecting rod, and an 2-1st output-side transmission link positioned at an opposite side of the 2-1st input-side transmission link,
   wherein the 2-2nd four links comprising a 2-2nd base link, a 2-2nd connecting rod positioned at an opposite side of the 2-2nd base link, an 2-2nd input-side transmission link connecting the 2-2nd base link to one end of the 2-2nd connecting rod, and an 2-2nd output-side transmission link positioned at an opposite side of the 2-2nd input-side transmission link, and wherein the 1st output link and the 2-2nd base link are movable integrally.

7. The link device according to claim 6,
wherein the moving trajectory of the 2-2nd base link is limited by the 1st ouptut link.

8. The link device according to claim 6,
wherein the 1st output link and the 2-2nd base link are movable with the same trajectory.

9. The link device according to claim 6,
wherein movement of the 1st output link is inputted to the 2-2nd base link.

10. The link device according to claim 6,
wherein in a case that external force is applied to the 1st input-side transmission link, the external force is transmitted to the 1st output link and the 2-2nd base link.

11. The link device according to claim 6,
wherein at least one of length between the 1st input-side transmission link and the 1st output-side transmission link, length between the 2-1st input-side transmission link and the 2-1st output-side transmission link or length between the 2-2nd input-side transmission link and the 2-2nd output-side transmission link is different.

12. The link device according to claim 6, further comprising,
a 1st joint between the 2-1st output-side transmission link and the 2-2nd input-side transmission link,
wherein a certain angle between the 2-1st output-side transmission link and the 2-2nd input-side transmission link is maintained by the 1st joint.

13. The link device according to claim 6, further comprising,
2nd output link connected to the 2nd position control section,
wherein a certain angle between the 2-2nd output-side transmission link and the 2nd output link is maintained by the 2nd joint.

14. The link device according to claim 6,
wherein the 1st external force is applied to the 1st input-side transmission link, and
wherein the 2nd external force is applied to the 2-1st input-side transmission link.

* * * * *